United States Patent [19]

Godfrey et al.

[11] Patent Number: 4,957,609
[45] Date of Patent: Sep. 18, 1990

[54] PROCESS FOR PREPARING N-HETEROCYCLIC COMPOUNDS

[75] Inventors: Neil Godfrey, Stevenage; Ian H. Coates, Hertford; James A. Bell, Ware; David C. Humber, Ealing; George B. Ewan, Chalfont St. Peter, all of England

[73] Assignee: Glaxo Group Limited, London, England

[21] Appl. No.: 312,172

[22] Filed: Feb. 21, 1989

Related U.S. Application Data

[63] Continuation of Ser. No. 888,256, Jul. 23, 1986, abandoned.

[30] Foreign Application Priority Data

Jul. 24, 1985 [GB] United Kingdom ............... 8518742

[51] Int. Cl.$^5$ ............... C07D 403/00; C07D 209/82; C07D 209/86
[52] U.S. Cl. ............... 204/157.71; 204/157.72; 548/336; 548/439; 548/447
[58] Field of Search ............... 548/336, 439, 447; 204/157.71, 157.72

[56] References Cited

U.S. PATENT DOCUMENTS 4,822,881 4/1989 Coates, et al. ............... 548/336

Primary Examiner—Mary C. Lee
Assistant Examiner—Robert C. Whittenbaugh
Attorney, Agent, or Firm—Bacon & Thomas

[57] ABSTRACT

The invention relates to a process for the preparation of compounds of general formula (I)

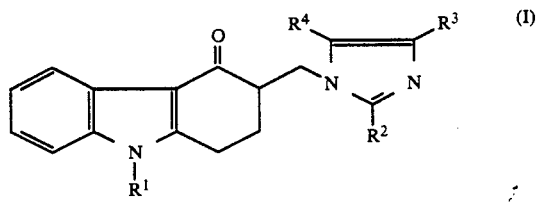

wherein
R$^1$ represents a hydrogen atom or a C$_{1-10}$ alkyl, C$_{3-7}$ cycloalkyl, C$_{3-7}$ cycloalkyl-(C$_{1-4}$)alkyl, C$_{3-6}$ alkenyl, C$_{3-10}$ alkynyl, phenyl or phenyl-(C$_{1-3}$)alkyl group, and one of the groups represented by R$^2$, R$^3$ and R$^4$ is a hydrogen atom or a C$_{1-6}$ alkyl, C$_{3-7}$ cycloalkyl, C$_{2-6}$ alkenyl or phenyl-phenyl-(C$_{1-3}$)alkyl group and each of the other two groups, which may be the same or different, represents a hydrogen atom or a C$_{1-6}$ alkyl group; or a salt or protected derivative thereof by cyclization of a compound of general formula (II)

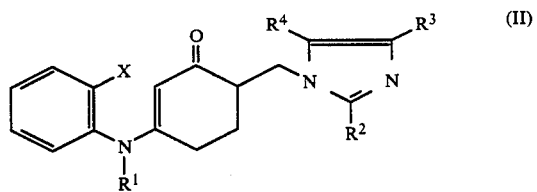

wherein X represents a hydrogen atom or a halogen atom and R$^1$, R$^2$, R$^3$ and R$^4$ are as defined above, or a salt or a protected derivative thereof.

The compounds of formula (I) are potent and selective antagonists at "neuronal" 5-hydroxytryptamine receptors.

10 Claims, No Drawings

PROCESS FOR PREPARING N-HETEROCYCLIC COMPOUNDS

This application is a continuation of application Ser. No. 888,256, filed Jul. 23, 1986, now abandoned.

This invention relates to improvements in or relating to a group of heterocyclic compounds. More particularly it relates to a process for their preparation.

In our British patent application No. 2153821A and European patent application No. 86300423 we describe 3-imidazolylmethyltetrahydrocarbazolones which may be represented by the general formula (I).

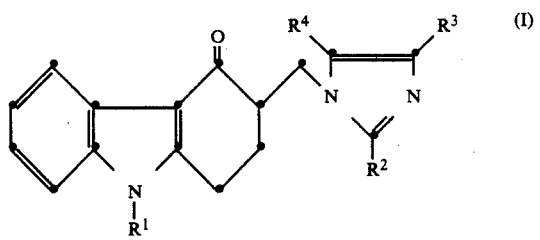

wherein $R^1$ represents a hydrogen atom or a $C_{1-10}$ alkyl, $C_{3-7}$ cycloalkyl, $C_{3-7}$cycloalkyl-$(C_{1-4})$alkyl, $C_{3-6}$ alkenyl, $C_{3-10}$ alkynyl, phenyl or phenyl-$(C_{1-3})$alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$(C_{1-3})$alkyl group and each of the other two groups, which may be the same or different, represents a hydrogen atom or a $C_{1-6}$ alkyl group;

and physiologically acceptable salts and solvates, e.g. hydrates, thereof. Several processes for the preparation of these compounds are also described in the above-mentioned patent applications.

The compounds of formula (I) are described in the aforementioned specifications as potent and selective antagonists at 'neuronal' 5-hydroxytryptamine (5HT) receptors, which are of use in the treatment of migraine pain and psychotic disorders such as schizophrenia. It is also stated that the compounds may be useful in the treatment of conditions such as anxiety, obesity and mania.

We have now devised a process for the preparation of the compounds of general formula (I), and salts and protected derivatives thereof in which a cyclisation reaction is used as the last major chemical step in the synthesis.

According to one aspect of the present invention, therefore, we provide a process for the preparation of a compound of general formula (I) or a salt or protected derivative thereof which comprises the step of cyclisation of a compound of general formula (II).

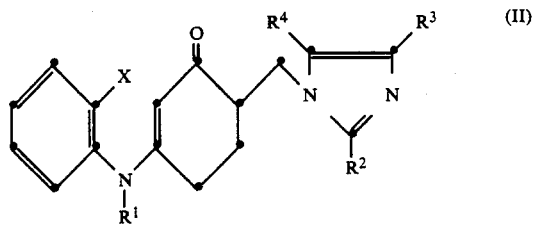

(wherein X represents a hydrogen atom or a halogen atom and $R^1$, $R^2$, $R^3$ and $R^4$ are as defined previously) or a salt or protected derivative thereof.

When X represents a halogen atom it may be, for example, a chlorine atom or, preferably, a bromine or iodine atom.

A protected derivative of general formula (II) may be for example a compound in which the carbonyl group is protected. The carbonyl protecting group may be a conventional carbonyl protecting group such as those described in 'Protective Groups in Organic Chemistry' Ed. J. F. W. McOmie (Plenum Press 1973) or 'Protective Groups in Organic Synthesis' by Theodora W. Greene (John Wiley and Sons, 1981). Thus, for example, it may be a ketal, such as a dialkyl or cyclic ketal formed with an appropriate alkylorthoformate or diol, a thioketal, a bisulphite addition complex or an enol ether.

The reaction may be effected in the presence of a palladium reagent, or, when X represents a halogen atom, in the presence of a copper (I) salt or photochemically.

The palladium reagent may be, for example, a palladium salt derived from an organic acid, e.g. an acetate such as palladium (II) acetate, or a trifluoroacetate, or derived from an inorganic acid, e.g. a chloride or bromide; a palladium complex such as a triarylphosphine palladium complex, e.g. a triphenylphosphine or tri(2-methylphenyl)phosphine palladium complex; or finely divided palladium metal such as palladium on charcoal. The triarylphosphine palladium complex may be generated in situ by reacting a palladium salt, e.g. palladium acetate, with the appropriate triarylphosphine.

When a palladium reagent is used in the above process, the reaction may be effected in the presence or absence of a solvent. Suitable solvents include nitriles, e.g. acetonitrile, alcohols e.g. methanol or ethanol, amides e.g. dimethylformamide, N-methylpyrrolidone or hexamethylphosphoramide, and water. The reaction may conveniently be carried out at a temperature of from 25° to 200° C., preferably 50° to 160° C.

When a compound of formula (II) in which X represents a halogen atom is employed, the palladium reagent is preferably used in the presence of a base. Only a catalytic quantity of the palladium reagent will then be required. Suitable bases include tertiary amines e.g. triethylamine or tri-n-butylamine, or alkali metal carbonates, bicarbonates and acetates, e.g. sodium or potassium carbonate, bicarbonate or acetate.

When a compound of formula (II) in which X represents a halogen atom other than an iodine atom, e.g. a chlorine or bromine atom is used, the palladium reagent, which may be generated in situ, is preferably a triarylphosphine palladium complex.

When a compound of formula (II) in which X represents a hydrogen atom is used, the palladium reagent is preferably a palladium salt. The reaction may conveniently be effected in the presence of an oxidising agent such as a copper (II) or silver salt e.g. cupric acetate or silver acetate in the presence of oxygen. Only a catalytic quantity of the palladium reagent will then be required.

A compound of general formula (II) wherein X represents a halogen atom may be cyclised according to the process of the present invention in the presence of a copper (I) salt. The copper (I) salt may be, for example, copper (I) iodide. The reaction will generally be effected in the presence of a strong base, e.g. an alkali metal hydride such as sodium hydride or an alkali metal alkoxide such as sodium ethoxide. Suitable solvents include amides, e.g. dimethylformamide, N-methylpyrrolidone or hexamethylphosphoramide, nitriles, e.g. acetonitrile, and alcohols, e.g. ethanol. The reaction may conveniently be effected at a temperature of 50° to 200° C., preferably 100° to 170° C.

When it is desired to effect the process of the invention photochemically, this may conveniently be achieved by irradiating for example with a mercury lamp, preferably a high pressure mercury lamp. Suitable solvents for the reaction include nitriles, e.g. acetonitrile, chlorinated hydrocarbons e.g. carbon tetrachloride, and cyclic ethers, e.g. tetrahydrofuran or dioxan. The reaction is conveniently effected in the presence of a base such as a tertiary amine, e.g. triethylamine.

The compounds of formula (II) may be prepared by reacting a compound of formula (III).

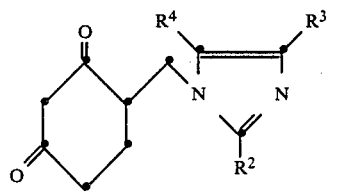
(III)

(wherein $R^2$, $R^3$ and $R^4$ are as defined previously) or a salt or protected derivative thereof with a compound of formula (IV):

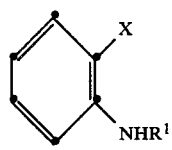
(IV)

(wherein X and $R^1$ are as defined previously) or a salt thereof.

The reaction may conveniently be effected in an aqueous solvent such as water.

A protected derivative of a compound of general formula (III) may for example have one or both of the carbonyl groups protected, e.g. as described above for protected derivatives of formula (II). It will be appreciated that when a compound of formula (III) is employed in which the carbonyl group which reacts with the aniline (i.e. the group furthest from the imidazolyl-methyl function) is protected, it may be necessary to remove the protecting group in order for reaction to occur with the compound of formula (IV). Deprotection may be effected by conventional procedures, for example as described hereinafter. If desired, deprotection may be effected in situ.

Alternatively the compounds of formula (II) wherein $R^1$ represents other than hydrogen may be prepared by alkylating a compound of formula (II) wherein $R^1$ represents a hydrogen atom with a compound of formula $R^{1a}Y$ in which $R^{1a}$ represents a $C_{1-10}$ alkyl, $C_{3-7}$ cycloalkyl, $C_{3-7}$ cycloalkyl-($C_{1-4}$)alkyl, $C_{3-6}$ alkenyl, $C_{3-10}$ alkynyl or phenyl $C_{1-3}$ alkyl group and Y represents a leaving atom or group such as a halogen atom, e.g. chlorine, bromine or iodine, or a hydrocarbylsulphonyloxy group e.g. p-toluenesulphonyloxy.

The reaction may conveniently be effected in the presence of a strong base such as an alkali metal hydride, e.g. sodium hydride, or an alkali metal alkoxide, e.g. sodium ethoxide.

Suitable solvents include alcohols, e.g. ethanol, ethers, e.g. tetrahydrofuran and amides, e.g. dimethylformamide.

The compounds of formula (III) may be prepared by reacting an imidazole of formula (V)

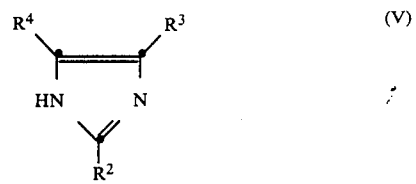
(V)

(wherein $R^2$, $R^3$ and $R^4$ are as defined previously) or a salt thereof with a compound of formula (VI)

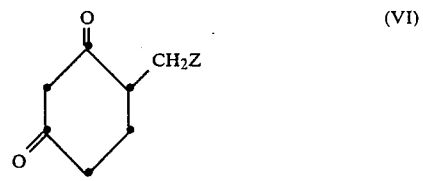
(VI)

(wherein Z represents a leaving atom or group, for example a halogen atom or the group $-N^+(CH_3)_3$ which will have an associated anion such as a halide ion, e.g. $I^-$) or a protected derivative thereof, e.g. a corresponding compound in which the carbonyl group at the 3-position is protected as described above for compounds of formula (III) (for example as an enol ether such as the methyl enol ether).

The reaction is conveniently effected in a suitable solvent such as water, an amide, e.g. dimethylformamide, a ketone, e.g. acetone or an ether, e.g. dioxan, and at a temperature of from 20° to 150° C.

The compounds of formula (VI) wherein Z represents the group $N^+(CH_3)_3I^-$ may be prepared by a Mannich reaction using a cyclohexane-1,3-dione derivative in which one of the carbonyl groups is protected (for example as the methyl enol ether) followed by methylation. Thus the protected dione may be reacted with formaldehyde and dimethylamine. More conveniently the cyclohexane-1,3-dione, in the form of an enolate, may be reacted with Eschenmoser's salt ($CH_2=N^+(CH_3)_2I^-$), followed by reaction with a methylating agent such as methyl iodide.

A compound of formula (VI) in which Z represents a halogen atom may be prepared for example by reacting cyclohexane-1,3-dione with formaldehyde in the presence of a base to give a compound of formula (VI) in which Z represents a hydroxy group, and reacting this with a halogenating agent such as phosphorus tribromide.

Where it is necessary and/or desired to effect deprotection of a compound at any stage in the reaction sequence, this may be effected using conventional techniques such as those described in 'Protective Groups in Organic Chemistry' Ed. J. F. W. McOmie (Plenum Press, 1973) or 'Protective Groups in Organic Synthesis' by Theodora W Greene (John Wiley & Sons 1981). Thus an enol ether may be hydrolysed in the presence of an aqueous acid, e.g. dilute sulphuric acid or hydrochloric acid. A ketal such as an alkyleneketal group may be removed by treatment with a mineral acid such as hydrochloric acid. A thioketal group may be cleaved by treatment with a mercuric salt, e.g. mercuric chloride, in a suitable solvent such as ethanol.

The compounds of formula (I) may be converted into their physiologically acceptable salts according to conventional methods. Thus, for example, the free base of general formula (I) may be treated with an appropriate acid, preferably with an equivalent amount, in a suitable solvent (e.g. aqueous ethanol).

Preferred compounds which may be prepared by the process of the present invention are compounds of general formula (I) wherein $R^1$ represents a hydrogen atom or a $C_{1-10}$ alkyl, $C_{3-7}$ cycloalkyl, $C_{3-6}$ alkenyl, phenyl or phenyl-$(C_{1-3})$-alkyl group, and $R^2$, $R^3$ and $R^4$ are as previously defined, and physiologically acceptable salts and solvates e.g. hydrates thereof.

Preferred compounds which may be prepared according to the process of the present invention are
1,2,3,9-tetrahydro-3-[(2-methyl-1H-imidazol-1-yl)methyl]-9-(2-propenyl)-4H-carbazol-4-one;
9-cyclopentyl-1,2,3,9-tetrahydro-3-[(2-methyl-1H-imidazol-1-yl)methyl]-4H-carbazol-4-one; and
1,2,3,9-tetrahydro-9-(1-methylethyl)-3-[(2-methyl-1H-imidazol-1-yl)methyl]-4H-carbazol-4-one and their physiologically acceptable salts and solvates.

A particularly preferred compound is 1,2,3,9-tetrahydro-9-methyl-3-[(2-methyl-1H-imidazol-1-yl)methyl]-4H-carbazol-4-one, and the physiologically acceptable salts and solvates (e.g. hydrates) thereof. A preferred form of this compound is the hydrochloride dihydrate.

The following Preparations and Examples illustrate the invention. All temperatures are in °C.

Chromatography was carried out either in the conventional manner using silica gel (Merck, Kieselgel 60, Art. 7734 or 7747) or by flash chromatography (W. C. Still, M. Kahn and A. Mitra, *J. Org. Chem.* 1978, 43, 2933) on silica (Merck 9385) and thin layer chromatography (t.l.c.) on silica (Macherly-Nagel, Polygram) except where otherwise stated. The following abbreviations define the eluent used for chromatography and t.l.c.

| (A) | Dichloromethane-ethanol-0.88 ammonia | 89:10:1 |
| (B) | Dichloromethane-ethanol-0.88 ammonia | 200:10:1 |
| (C) | Dichloromethane-ethanol-0.88 ammonia | 94.5:5:0.5 |
| (D) | Dichloromethane-ethanol-0.88 ammonia | 91.7:7.5:0.8 |
| (E) | Ether-methanol | 95:5 |
| (F) | Ether-methanol | 90:10 |
| (G) | Dichloromethane-ethanol-0.88 ammonia | 83.5:15:1.5 |

Intermediates were checked for purity by t.l.c. employing u.v. light for detection and spray reagents such as a solution of iodoplatinic acid (IPA).

Proton ($^1$H) nuclear magnetic resonance (n.m.r.) spectra were obtained either at 90 MHz using a Varian EM 390 instrument or at 250 MHz using a Bruker AM or WM 250 instrument. s=singlet, d=doublet, t=triplet, m=multiplet, q=quartet, and br=broad.

Intermediate 1

6-[(Dimethylamino)methyl]-3-methoxy-2-cyclohexen-1-one maleate n-Butyllithium (1.55M in hexane, 32.3 ml) was added to a stirred solution of dry diisopropylamine (7.0 ml) in dry tetrahydrofuran (60 ml) at −70° under nitrogen, and stirring was continued for 10 min. A solution of 3-methoxy-2-cyclohexen-1-one (5.0 g) in dry THF (10 ml) was added dropwise over 10 min, and stirring was continued at −70° to −60° for 40 min. The mixture was transferred by a double ended needle to a second flask containing a stirred suspension of N,N-dimethylmethylene ammonium iodide (Eschenmoser's salt) (13.9 g) in dry THF (40 ml) at −60°, and the mixture was allowed to warm to 0° with stirring over 4 h, and allowed to stand at room temperature overnight. The mixture was poured into 8% aqueous sodium bicarbonate (200 ml), further basified with 2N sodium hydroxide (100 ml), saturated with sodium chloride, and extracted with ether (4×200 ml). The organic layers were washed with brine, dried (MgSO$_4$) and evaporated to give an oil (7.65 g). Purification by short path chromatography (A) gave the free base as an oil (3.94 g). A portion of the oil (187 mg) was dissolved in methanol (1 ml), maleic acid (124 mg) in methanol (1 ml) was added and the solution was diluted with dry ether (70 ml), giving a precipitate, which was filtered off, washed with ether and dried (in vacuo at room temperature) to present the title compound as a solid (283 mg), m.p. 132°–134°.

Intermediate 2

3-Methoxy-6-[(2-methyl-1H-imidazol-1-yl)methyl]-2-cyclohexen-1-one maleate

Iodomethane (1.27 ml) was added to a stirred solution of Intermediate 1 as the base (3.7 g) in dry N,N-dimethylformamide (80 ml) at room temperature under nitrogen, and stirring was continued at room temperature for 25 min. 2-Methylimidazole (8.4 g) was added, and the mixture was heated at 80° for 4 h. The mixture was poured into brine (250 ml) and extracted with ethyl acetate (3×250 ml). The organic layers were washed with brine (3×250 ml) and the combined aqueous layers further extracted with ethyl acetate (3×400 ml). The combined organic layers were dried (MgSO$_4$) and evaporated to give a semi-solid (10.5 g). Purification by flash chromatography (A) gave the product as an oil which slowly crystallised (3.60 g). A sample (165 mg) was dissolved in methanol (0.5 ml), and maleic acid (91 mg) was added. Addition of dry ether (25 ml) gave a precipitate which was filtered off, washed with dry ether and dried (in vacuo at room temperature) to present the title compound as a solid (192 mg), m.p. 134.5°–135.5°.

Intermediate 3

3-[(2-Iodophenyl)amino]-2-cyclohexen-1-one

A stirred mixture of 2-iodoaniline (22.2 g) and cyclohexane-1,3-dione (11.2 g) was heated under nitrogen at 120° for 1 h, cooled and the resulting solid pulverised under ether (300 ml). The mixture was filtered and the solid (30 g) recrystallised from acetone:hexane (1:1, 400 ml), giving the title compound as prisms m.p. 151°–3° (decomp.).

EXAMPLE 1

1,2,3,9-Tetrahydro-3-[(2-methyl-1H-imidazol-1-yl)methyl]4H-carbazol-4-one (i)

3-[(2-Iodophenyl)amino]-6-[(2-methyl-1H-imidazol-1-yl)methyl]-2-cyclohexen-1-one 2M Hydrochloric acid (4.5 ml) was added with stirring to a solution of Intermediate 2, as the free base (900 mg) in water (25 ml). After 3.75 h, 2-iodoaniline (5.00 g) was added, and after a further 18 h, the suspension was partitioned between 8% aqueous sodium bicarbonate (100 ml) and ethyl acetate (3×100 ml). The combined, dried (Na2SO4) organic extracts were evaporated and the residue purified by flash chromatography (B) to give a solid, which was heated in vacuo for 17 h, to give the title compound as a foam (970 mg), m.p. 88°–100°.

Analysis Found: C,49.2; H,4.3; N,9.9 $C_{17}H_{18}IN_3O.0.02EtOH$ requires: C,50.1; H,4.5; N,10.3%

(ii) 1,2,3,9-Tetrahydro-3-[(2-methyl-1H-imidazol-1-yl)methyl]-4H-carbazol-4-one A stirred mixture of the product of Stage (i) (200 mg), palladium (II) acetate (4.4 mg), tri-(2-methylphenyl) phosphine (11.9 mg), sodium bicarbonate (83 mg) and DMF (4 ml) were heated under nitrogen at 120° for 20 h. When cool, the reaction mixture was evaporated, treated with water (15 ml), extracted with chloroform (3×20 ml), and the combined, dried (Na2SO4) extracts were evaporated. The residue was purified by short path chromatography (C) and (D) to give the title compound as a solid (5.5 mg) which was shown by n.m.r. and t.l.c. (A) to be identical with the product of Example 3b in British patent application No. 2153821A.

EXAMPLE 2

(i) 3-[(2-Iodophenyl)methylamino]-2-cyclohexen-1-one

A suspension of Intermediate 3 (7.35 g) in dry benzene (50 ml) was added to a stirred suspension of sodium hydride (1.42 g of a 76% dispersion in oil) in dry benzene (100 ml) at room temperature under nitrogen and the mixture heated at reflux for 1 h. After cooling to 0°, methyl iodide (2.92 ml) was added, followed by a further period of heating at reflux (0.5 h). The cooled reaction mixture was poured onto saturated ammonium chloride solution (200 ml) and the layers separated. The aqueous layer was further extracted with ethyl acetate (3×100 ml) and the combined organic extracts dried (Na2SO4) and evaporated in vacuo. The residual oil (ca 8 g) was purified by flash chromatography (E) and (F) giving the title compound (6.3 g) as a crystalline solid m.p. 104°–6°.

(ii) 6-[(Dimethylamino)methyl]-3-[(2-iodophenyl)methylamino]-2-cyclohexen-1-one hydrochloride A solution of lithium diisopropylamide was made by the addition of n-butyllithium (nominally 1.5M in hexane, 1.73 ml) to a solution of diisopropylamine (0.36 ml) in dry tetrahydrofuran (20 ml) under nitrogen. This solution was added dropwise to a stirred solution of the product of Stage (i) (0.773 g) in dry tetrahydrofuran (30 ml) at −70° under nitrogen. After 2 h at −70°, this solution was added dropwise via a double ended needle to a stirred suspension of dimethylaminomethylene iodide (Eschenmoser's salt, 0.873 g) in dry tetrahydrofuran at −70° under nitrogen. The mixture was stirred for 4 h while warming to room temperature, and then stood at room temperature for 72 h. The reaction mixture was evaporated in vacuo and the oily residue partitioned between saturated potassium carbonate (100 ml) and ethyl acetate (2×100 ml). The combined organic layers were dried (Na2SO4), evaporated in vacuo, triturated with ether (300 ml) and evaporated in vacuo, to give an oil (ca. 0.7 g). This oil was purified by flash chromatography (G) to give the free base (0.32 g) as a gum. A portion of the gum (240 mg) was dissolved in ethanol (4 ml) and ethereal hydrochloric acid added until a colour change from yellow to pink-red occurred. Further dilution with dry ether (ca. 50 ml) precipitated the title compound (185 mg) as a solid m.p. 141°–2° (decomp.).

(iii) 3-[(2-Iodophenyl)methylamino]-6-[(2-methyl-1H-imidazol-1-yl)methyl]-2-cyclohexen-1-one A mixture of the product of Stage (ii) (350 mg) and 2-methylimidazole (350 mg) in dry dimethylformamide (25 ml) was heated at 100° under nitrogen for 24 h. The cooled reaction mixture was evaporated in vacuo and purified by flash chromatography (C) to give, as the second eluted major component, the title compound (153 mg) as a gum. T.l.c. (C), Rf 0.35

(iv) 1,2,3,9-Tetrahydro-9-methyl-3-[(2-methyl-1H-imidazol-1-yl)methyl]-4H-carbazol-4-one A solution of the product of Stage (iii) (15 mg) and palladium (II) acetate (5 mg) in triethylamine (0.2 ml) and acetonitrile (0.1 ml) was heated under nitrogen in a sealed vessel for 1.75 h. The cooled reaction mixture was partitioned between potassium carbonate solution (15 ml) and dichloromethane (3×10 ml) and the combined organic layers were dried (Na2SO4) and evaporated in vacuo to leave a solid (12 mg). This material was purified by column chromatography (C) to give the title compound (6.3 mg) as a solid m.p. 215°–16° (decomp). The product was shown by n.m.r. and t.l.c. (A) Rf 0.47, to be identical to the product of Example 1a (as the free base) in British patent application No. 2153821A.

We claim:

1. A process for the preparation of a compound of formula (I)

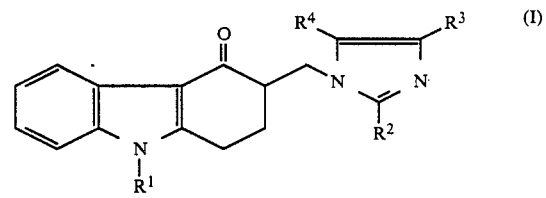

wherein $R^1$ represents a hydrogen atom or a $C_{1-10}$ alkyl, $C_{3-7}$ cycloalkyl, $C_{3-7}$ cycloalkyl-($C_{1-4}$)alkyl, $C_{3-6}$alkenyl, $C_{3-10}$alkynyl, phenyl or phenyl-($C_{1-3}$)alkyl group, and one of the groups represented by $R^2$, $R^3$, and $R^4$ is a hydrogen atom or a $C_{1-6}$alkyl, $C_{3-7}$ cycloalkyl, $C_{2-6}$alkenyl or phenyl-($C_{1-3}$)alkyl group and each of the other two groups, which may be the same or different, represents a hydrogen atom or a $C_{1-6}$alkyl group;

or a salt or protected derivative thereof which comprises the step of cyclisation of a compound of formula (II)

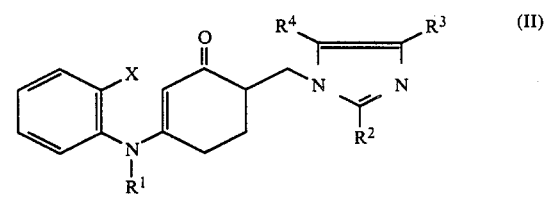

wherein X represents a hydrogen atom or a halogen atom and $R^1$, $R^2$, $R^3$ and $R^4$ are as defined above, or a salt or a protected derivative thereof, and wherein the cyclisation is carried out in the presence of a palladium reagent or, alternatively, where X represents a halogen atom, the cyclisation may be carried out in the presence of a copper (I) salt or photochemically.

2. A process as claimed in claim 1 for the production of a compound which is:

1,2,3,9-tetrahydro-3-[(2-methyl-1H-imidazol-1-yl)methyl]-9-(2-propenyl)-4H-carbazol-4-one;

9-cyclopentyl-1,2,3,9-tetrahydro-3-[(2-methyl-1H-imidazol-1-yl)methyl]-4H-carbazol-4-one;

1,2,3,9-tetrahydro-9-(1-methylethyl)-3-[(2-methyl-1H-imidazol-1-yl)methyl]-4H-carbazol-4-one) or a physiologically acceptable salt or solvate thereof.

3. A process as claimed in claim 1, wherein the compound of formula (I) is produced in the form of a protected derivative and the protecting group or groups are subsequently removed to produce the compound of formula (I) and/or the compound of formula (I) is produced in the form of the free base and the free base is subsequently converted into a salt.

4. A process as claimed in claim 1 wherein said palladium reagent is a palladium salt derived from an organic acid or an inorganic acid, a palladium complex or finely divided palladium metal.

5. A process as claimed in claim 1 wherein cyclisation is carried out in a solvent selected from the group consisting of nitriles, alcohols and amides.

6. A process as claimed in claim 1 wherein X is halogen and said palladium reagent is used in the presence of base.

7. A process as claimed in claim 1 wherein X is a halogen atom other than iodine and said palladium reagent is a triarylphosphine palladium complex.

8. A process as claimed in claim 1 wherein X is hydrogen and said palladium reagent is a palladium salt.

9. A process as claimed in claim 1 for the production of a compound of formula (I) in which $R^1$ represents a hydrogen atom or a $C_{1-10}$ alkyl, $C_{3-7}$ cycloalkyl, $C_{3-6}$ alkenyl, phenyl or phenyl-($C_{1-3}$)-alkyl group, and $R^2$, $R^3$ and $R^4$ are as defined in claim 1 or a physiologically acceptable salt or solvate thereof.

10. A process as claimed in claim 1 for the production of 1,2,3,9-tetrahydro-9-methyl-3-[(2-methyl-1H-imidazol-1-yl)methyl]-4H-carbazol-4-one or a physiologically acceptable salt or solvate thereof.

* * * * *